United States Patent
Koerber et al.

(10) Patent No.: US 10,508,982 B2
(45) Date of Patent: Dec. 17, 2019

(54) PARTICLE SENSOR AND PARTICLE SENSING METHOD

(71) Applicant: KONINKLIJKE PHILIPS N.V., Eindhoven (NL)

(72) Inventors: Achim Gerhard Rolf Koerber, Eindhoven (NL); Rainer Hilbig, Aachen (DE); Cornelis Reinder Ronda, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 29 days.

(21) Appl. No.: 15/736,832

(22) PCT Filed: Jun. 29, 2016

(86) PCT No.: PCT/EP2016/065072
§ 371 (c)(1),
(2) Date: Dec. 15, 2017

(87) PCT Pub. No.: WO2017/005560
PCT Pub. Date: Jan. 12, 2017

(65) Prior Publication Data
US 2018/0164203 A1    Jun. 14, 2018

(30) Foreign Application Priority Data
Jul. 3, 2015  (EP) .................... 15175272

(51) Int. Cl.
*G01N 15/02*   (2006.01)
*B03C 3/06*    (2006.01)
(Continued)

(52) U.S. Cl.
CPC ......... *G01N 15/0266* (2013.01); *B03C 3/017* (2013.01); *B03C 3/06* (2013.01);
(Continued)

(58) Field of Classification Search
CPC .......... G01N 15/0266; G01N 15/0656; G01N 2015/0038; G01F 5/005; B03C 3/45;
(Continued)

(56) References Cited

U.S. PATENT DOCUMENTS

| | | | |
|---|---|---|---|
| 4,769,609 A * | 9/1988 | Masuda ............. | G01N 15/0266 324/455 |
| 2008/0041138 A1* | 2/2008 | Marra ................... | B60H 1/008 73/31.02 |
| 2012/0174650 A1* | 7/2012 | Ariessohn ................ | B08B 3/12 73/23.2 |

FOREIGN PATENT DOCUMENTS

EP      2134556 B1    7/2012
WO    WO2008122932 A1  10/2008

OTHER PUBLICATIONS

Marra, J., "Ionic Wind Sensor for Detecting Airborne Ultrafine Particles", Philips Research Europe, Technical Note PR-TN 2010/00043, Issued: Jan. 2010.

* cited by examiner

*Primary Examiner* — Farhana A Hoque

(57) ABSTRACT

A particle sensor uses an electrostatic particle charging section in the form of an ionization chamber. A flow sensor arrangement is used to produce a signal which is representative of the amount of gas flow between the outside of the ionization chamber and the inside of the ionization chamber. This information is indicative of the flow conditions, and can be used to determine when adverse flow conditions are present which may adversely affect the performance or lifetime of the particle sensor.

17 Claims, 3 Drawing Sheets

(51) Int. Cl.
*B03C 3/12* (2006.01)
*G01N 15/06* (2006.01)
*B03C 3/017* (2006.01)
*B03C 3/36* (2006.01)
*B03C 3/41* (2006.01)
*B03C 3/49* (2006.01)
*B03C 3/45* (2006.01)
*G01F 5/00* (2006.01)
*G01N 15/00* (2006.01)

(52) U.S. Cl.
CPC ............... *B03C 3/12* (2013.01); *B03C 3/368* (2013.01); *B03C 3/41* (2013.01); *B03C 3/45* (2013.01); *B03C 3/49* (2013.01); *G01F 5/005* (2013.01); *G01N 15/0656* (2013.01); *G01N 2015/0038* (2013.01)

(58) Field of Classification Search
CPC .. B03C 3/49; B03C 3/41; B03C 3/368; B03C 3/017; B03C 3/06; B03C 3/12
USPC ......................................... 324/464; 73/31.02
See application file for complete search history.

PARTICLE SENSOR AND PARTICLE SENSING METHOD

FIELD OF THE INVENTION

This invention relates to particle sensors, in particular ultrafine particle sensors that operate based on the principle of measuring an electrical current that results from the precipitation of ultrafine particles that have been electrically charged by diffusion charging.

BACKGROUND OF THE INVENTION

Diffusion charging refers to a particle charging process wherein airborne particles are electrically charged in a particle charging section by collisions with gaseous ions (typically positive ions) that have been generated by an ionization electrode such as a needle-tip electrode or corona wire.

A known particle sensor of this type typically comprises a means for establishing an airflow through the sensor (for example a ventilator, a fan or a pump). The airflow passes through the particle charging section, and then through a particle precipitation section for removing substantially all airborne particles from the flow.

The sensor further comprises a particle measurement section having a current meter for measuring the electrical current that results from the deposition of particle-bound charge per unit time in the particle precipitation section.

From the measured electrical current a so-called apparent ultrafine particle number concentration can be calculated. The apparent ultrafine particle number concentration is equal to the ratio of the particle length concentration (i.e. the total length of the string of all airborne UFPs in a unit air volume when they would be lined up therein as a string) and a predetermined average particle diameter.

The particle precipitation section may comprise a mechanical particle filter disposed within a Faraday cage, or a parallel-plate electrostatic particle precipitator. In the case of a parallel-plate electrostatic particle precipitator, charged positive particles are precipitated at the negative plate of the capacitor and the resulting current measured is proportional to the particle concentration times particle diameter.

The particle charging section of the ultrafine particle sensor is for example designed with a high voltage ionization electrode in the form of a needle-tip electrode that is surrounded by an electrically conductive enclosure. The enclosure is at least partly provided with openings. By applying a potential difference between the needle-tip electrode and the electrically conductive enclosure, gaseous ions can be generated that are drawn from the needle-tip electrode towards the enclosure, to escape through the openings establishing a region containing gaseous ions next to the enclosure. The enclosure forms a corona ionization chamber and the gaseous ions emanate through a metal grid into the adjacent gas flow channel.

When an air flow carrying the ultrafine particles passes through this region the airborne particles are electrically charged by diffusion charging.

It turns out that for such a construction, the performance of the needle-tip electrode reduces over time. It has been found out that this is due to a contamination of the electrode's outer surface by compounds that are present in the surroundings of the electrode. For example, silane compounds may form a silicon dioxide layer on the outer surface of the ionization electrode which acts as an electrically insulating layer. Such contaminants are typically present in the airflow carrying the ultrafine particles that are to be monitored.

SUMMARY OF THE INVENTION

The invention is defined by the claims.

According to examples in accordance with an aspect of the invention, there is provided a particle sensor, comprising:

an input for receiving a gas flow with entrained particles;

an electrostatic particle charging section comprising an ionization electrode within an ionization chamber, wherein the gas flow passes past the ionization chamber and partially enters the ionization chamber;

a particle precipitation section; and a sensor unit for detecting the precipitated particles to produce a sensor signal, wherein the particle sensor comprises a sensor arrangement for producing a signal which is representative of the amount of gas flow between the outside of the ionization chamber and the inside of the ionization chamber.

The invention is based on the recognition that although the ionization electrode is separated from the main airflow by the outer enclosure of the ionization chamber, at least a part of the air flow can still enter the enclosure via openings in this enclosure, as a result of an electrohydrodynamic phenomenon called the "ionic wind". The repulsion of gaseous ions from the ionization electrode creates an expanding ion cloud, which in turn creates this ionic wind emanating from the electrode. A pressure difference resulting from the presence of this wind can cause at least part of the airflow to enter through the openings into the enclosure thereby exposing the ionization electrode to harmful contaminants.

This ionic wind within the ionization chamber in particular leads to a gas flow redistribution so that a large fraction (or all) of the gas flow is travelling through the ionization chamber. In operation, the performance of the ionization electrode will gradually decrease over time as a result of being exposed to contamination from the airflow. This performance decrease can be manifested as flow instabilities, ionization electrode (i.e. corona needle) lifetime problems and loss of charged particles.

This situation may even arise when a pre-filter such as an activated carbon filter is used, because such a filter will not remove all harmful contaminants and/or will deteriorate over time. To ensure proper operating conditions, the voltage applied to the ionization electrode may be adjusted to compensate for this decrease in performance. However, increasing the voltage will typically result in a stronger ionic wind that pulls in more of the airflow, and when the voltage is increased beyond a certain level the performance will suddenly decrease very strongly.

The invention provides a sensor system for producing a signal which is representative of the amount of gas flow between the outside of the ionization chamber and the inside of the ionization chamber. When the signal exceeds a predetermined threshold level, the magnitude of the ionic wind and/or the flow rate of the airflow may be adjusted. In this way, the operational lifetime of the device is increased.

In one set of examples, the sensor arrangement comprises an arrangement of flow rate meters. These flow meters measure the flow rate of the airflow. By measuring flow rate conditions at different locations, the flow conditions can be determined.

For example, the arrangement of flow meters may comprise a first flow meter outside the ionization chamber in the vicinity of an inlet end and/or an outlet end of the particle charging section, and a second flow meter outside the ionization chamber in the vicinity of a tip of the ionization electrode.

The flow rate outside the ionization chamber but nearest the ionization electrode (i.e. laterally to the side of the ionization electrode) will have the greatest change in reading when there is a change in the amount of flow between the inside and the outside of the ionization chamber. The second flow meter is for example between the inlet end of the particle charging section and the tip of the ionization electrode. The greatest change in flow rate is at the inlet side (i.e. just before) the ionization electrode.

When the air flow rate drops below a predetermined threshold level (relative to the general flow rate through the device as measured by the first flow meter), the airflow is considered to be pulled in to the enclosure too strongly, indicative of disturbed flow.

In a second set of examples, the sensor arrangement comprises an arrangement of pressure sensors. By measuring pressure conditions at different locations, the flow conditions can be determined.

For example, the arrangement of pressure sensors may comprise a first pressure sensor inside the ionization chamber and a second pressure sensor outside the ionization chamber.

The first pressure sensor may be at the inlet end of the ionization chamber and the second pressure sensor may be at the outlet end of the particle charging section.

The pressure difference as measured by the first and second pressure sensors may then be determined. When the pressure difference exceeds a predetermined threshold level, the airflow is again considered to be pulled in to the enclosure too strongly.

In each case, the particle sensor may further comprise a controller for controlling the drive level applied to the ionization electrode. The controller is adapted to select the drive level in dependence on the signal. In particular, when the flow conditions indicate that there is too large a flow into the ionization chamber, the drive level may be reduced.

The particle sensor may instead or additionally comprise a controller for controlling a flow rate through the particle sensor, and the flow rate is selected in dependence on the signal. In particular, when the flow conditions indicate that there is too large a flow into the ionization chamber, the flow rate may be reduced.

The precipitation section may comprise a parallel-plate particle precipitation section.

A non-metallic shield may be provided in the ionization chamber. This non-metallic shield may be provided to direct the ion flow produced near the needle-tip electrode towards the grid separating the ionization chamber from the flow channel.

The particle sensor may comprise a pre-filter to remove harmful contaminants (such as larger particles) from the airflow. The output of the sensor system may then also be used to determine when the pre-filter has deteriorated to such an extent that it should be replaced, by measuring the decrease in gas flow through the main channel. When the gas flow is reduced by a predetermined factor (for example by a factor of two), an indication can be given to the consumer that the filter needs to be replaced.

Examples in accordance with another aspect of the invention provide a particle sensing method, comprising:
receiving a gas flow with entrained particles;
passing the gas flow through an electrostatic particle charging section comprising an ionization electrode within an ionization chamber, wherein the gas flow is provided past the ionization chamber but partially enters the ionization chamber;
using a particle precipitation section, detecting the charge of the precipitated particles to produce a sensor signal; and
generating a signal which is representative of the amount of gas flow between the outside of the ionization chamber and the inside of the ionization chamber.

This method generates a signal which can be used to assess when flow conditions in and around the ionization chamber have become unsuitable, so that corrective action may be taken.

Generating a signal may comprise measuring a first flow rate outside the ionization chamber in the vicinity of an inlet end and/or an outlet end of the particle charging section, and measuring a second flow rate outside the ionization chamber in the vicinity of a tip of the ionization electrode, wherein the signal is based on the relative magnitudes of the first and second flow rates.

Generating a signal may instead comprise measuring a first pressure inside the ionization chamber and a second pressure sensor outside the ionization chamber, wherein the signal is based on the difference between the first and second pressures.

A drive signal to the ionization electrode may then be adjusted in response to the signal and/or the flow rate through the particle sensor may be controlled.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a particle sensor which uses an electrostatic particle charging section in the form of an ionization chamber. A flow sensor arrangement is used to produce a signal which is representative of the amount of gas flow between the outside of the ionization chamber and the inside of the ionization chamber. This information is indicative of the flow conditions, and can be used to determine when flow conditions are present which may adversely affect the performance or lifetime of the particle sensor.

The design and operation of known electrical ultra-fine particle (UFP) sensors will first be described in more detail. These sensors for example measure particles in the particle size range between approximately 10 nm and 500 nm. These sensors are for example used for the automatic control of air handling units in buildings or vehicle interiors, intended to supply fresh ventilation air while minimizing the indoor exposure to air pollutants.

Figure 1:
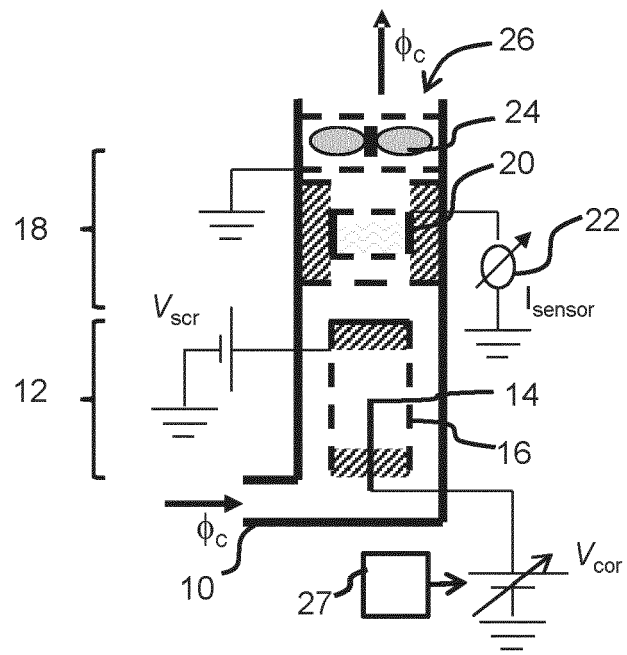
FIG. 1 shows a first known example of a particle sensor.

The most basic sensor implementation is shown in FIG. 1.

The sensor comprises an inlet 10 for receiving air at a flow rate $\phi_C$.

A UFP charging section 12 comprises an air-ionizing high voltage ionization electrode 14 surrounded by a porous screen electrode 16.

Further downstream is a UFP precipitation section 18 comprising a Faraday cage 20 containing a particle filter that is capable of substantially filtering all airborne particles from the sampled airflow that passes through the UFP sensor.

A current meter 22 is connected to the Faraday cage. It measures the amount of particle-bound charge that deposits per unit time inside the Faraday cage as an electrical current $I_{sensor}$. $I_{sensor}$ constitutes the sensor signal.

There is a means 24 for moving a sampled airflow comprising the airborne UFPs through the sensor. This can be a ventilator, fan, pump, or an ionic wind device. There is an air flow outlet 26 which expels air at the flow rate $\phi_C$.

The ionization is created by the high voltage $V_{cor}$ applied to the high voltage ionization electrode 14. The voltage is variable, under the control of a controller 27.

The inferred apparent UFP number concentration $N_{app}$ (as defined above) in the sampled airflow relates to the measured signal $I_{sensor}$ according to:

$$N_{app} = S \times I_{sensor} \quad (1)$$

S is a calibration constant, which is substantially independent of the specifics of the particle size distribution and thus substantially independent of the count mean UFP diameter $d_{p,av}$. Furthermore, the apparent particle number concentration $N_{app}$ is defined as:

$$N_{app} = \frac{N d_{p,av}}{d^*_{p,av}} \quad (2)$$

N is the total UFP number concentration, $d_{p,av}$ is the count mean particle diameter, and $d^*_{p,av}$ can be any pre-chosen default average particle diameter (usually $d^*_{p,av}$=50 nm).

Thus, $N_{app}$ is proportional to the product of N and $d_{p,av}$. The product $Nd_{p,av}$ denotes the particle length concentration (m/m³). Knowledge of only $N_{app}$ is sufficient to assess the relative severity of the UFP-associated air pollution level. Separate knowledge of both N and $d_{p,av}$ is not required for that purpose.

Equation 2 is valid for an average UFP particle size range 25 nm≤$d_{p,av}$≤120 nm. This range encompasses the typically encountered UFP size distributions throughout the UFP diameter range 10 nm≤$d_p$≤500 nm.

Figure 2:
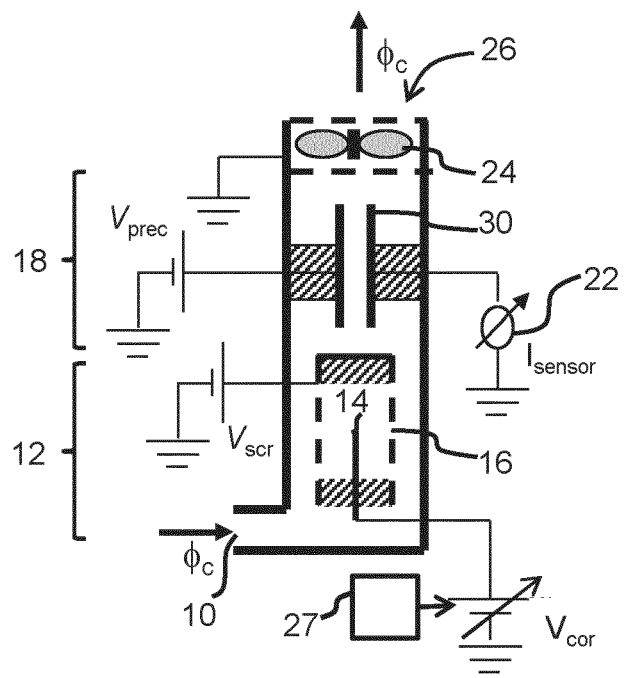
FIG. 2 shows a second known example of a particle sensor.

Instead of the UFP sensor embodiment shown in FIG. 1, an alternative embodiment in FIG. 2 can be used.

The same reference numbers are used as in FIG. 1 for the same components. Instead of the Faraday cage 20, a parallel-plate electrostatic particle precipitator 30 is provided and the current meter 22 is attached to the plate electrode whereupon the charged particles are precipitated. The parallel-plate precipitator can, for example, be embodied as two parallel flat electrode plates or as a concentric electrode set comprising an inner electrode that is surrounded by an outer electrode. Alternative embodiments will be apparent by the person skilled in the art.

Use of the embodiment in FIG. 2 instead of the embodiment in FIG. 1 is preferred for ease-of-assembly reasons when UFP sensors are to be mass-produced at low cost and small size.

The invention relates to the detection and/or prevention of undesired flow conditions in the ionization chamber.

Figure 3:
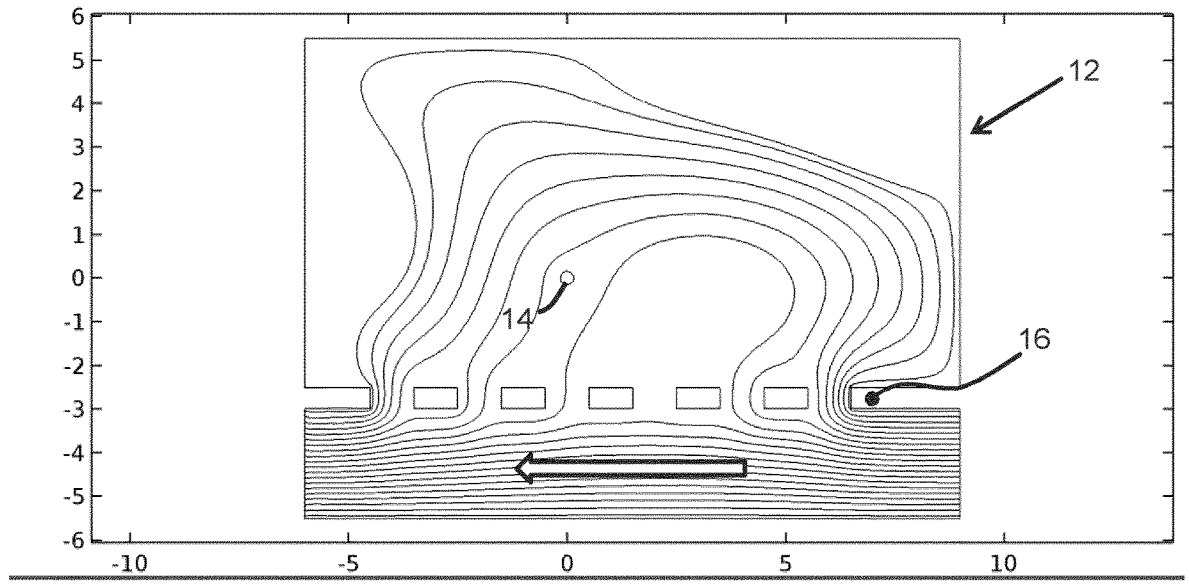
FIG. 3 shows first flow conditions in and around the particle charging section.

FIG. 3 shows an example of a desired gas flow situation within the particle charging section 12. The axes are in units of mm. The main gas flow channel is at the bottom of the figure with flow entering from the right and exiting to the left. The ionization chamber is located above the metal grid 16 (which is vertically at −2.75 mm, with the tip of the high voltage ionization electrode 14 used as the origin). Only a small fraction of the gas flow is travelling through the ionization chamber.

Figure 4:
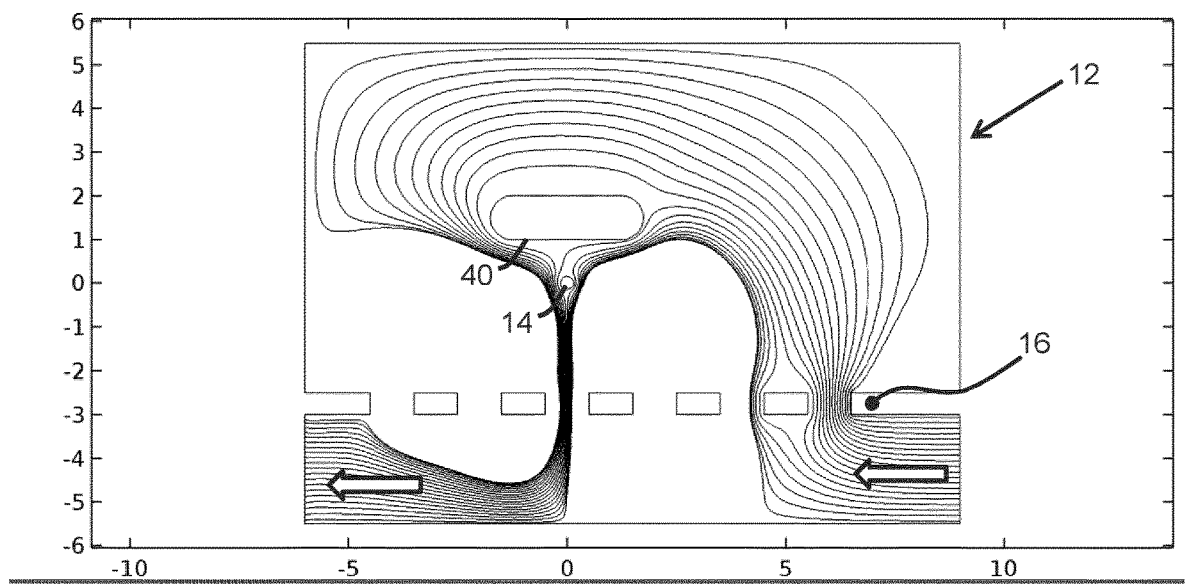
FIG. 4 shows second flow conditions in and around the particle charging section.

FIG. 4 shows an example of an undesired gas flow situation within the particle charging section 12. This flow pattern has been created by adding an oval metal shield 40 above the high voltage electrode 14, at a vertical location of +1.5 mm, and at the same potential as the high voltage ionization electrode 14. The shield blocks the upward pointing part of the ion current and is therefore creating a strongly asymmetric "ionic wind" force field which is oriented downwards only. This is a known approach.

The analysis of the flow conditions shows that the complete gas flow then travels through the ionization chamber.

Ion currents and gas velocities are identical in both examples.

FIG. 4 shows that a metallic shield is strongly disadvantageous when the flow conditions are considered, since it raises the operating voltage of the corona discharge device by several kilovolts. Furthermore it leads to a strongly directional flow of "ionic wind" and as a consequence to a dramatic increase of gas flow from the flow channel through the ionization chamber.

Figure 5:
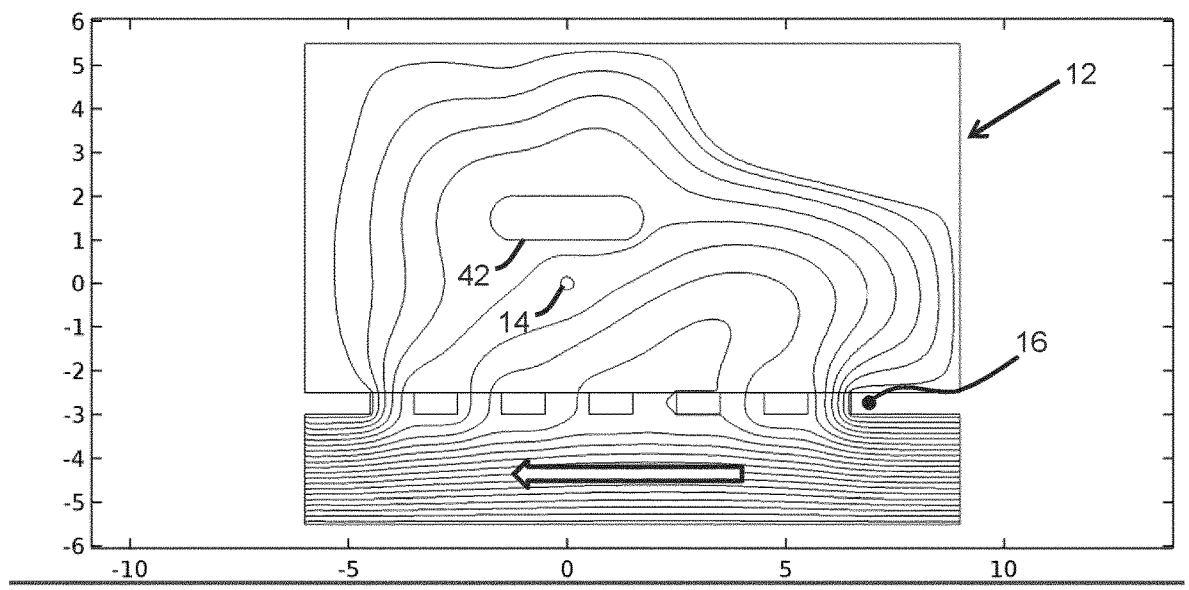
FIG. 5 shows third flow conditions in and around the particle charging section.

FIG. 5 shows that if a non-conducting shield 42 is used above the high voltage electrode 14, the change to the flow pattern is much less significant. Thus, the use of a non-metallic shield, for the same purpose as the metallic shield, is greatly preferred. The invention relates to measures to detect and prevent disadvantageous flow conditions.

A first aspect relates to the detection of undesired flow conditions.

A first approach is to measure the flow velocity in the center of the main gas flow channel (for example the region 1 mm<x<4 mm in FIGS. 3 to 5).

This velocity should not be less than a set fraction of the velocity at the entrance or exit of the main flow channel. This set fraction may for example be in the range 0.4 to 0.7, for example 0.4, 0.5 or 0.6.

Figures 6, 7:
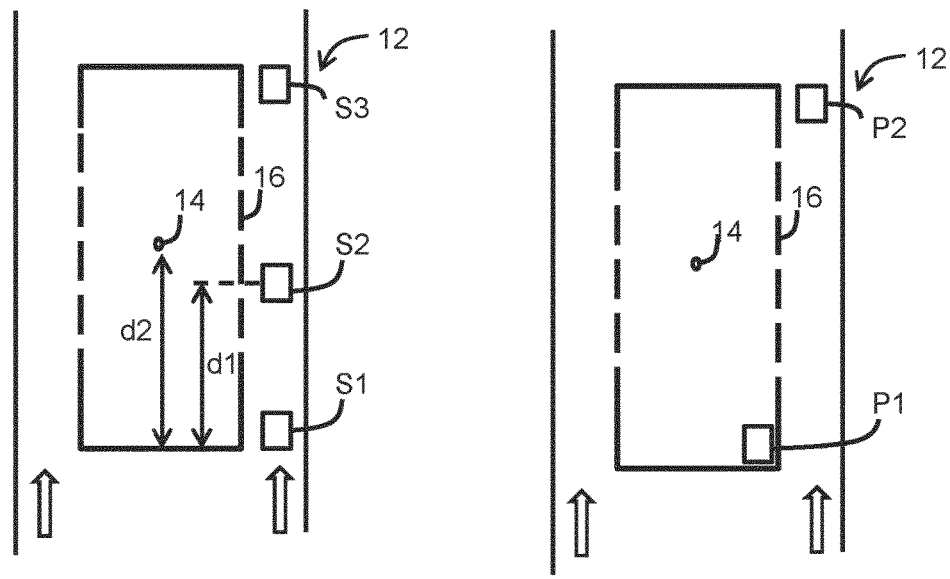
FIG. 6 shows a first example of flow sensor arrangement which may be used to modify the sensor of FIG. 1 or 2.
FIG. 7 shows a second example of flow sensor arrangement which may be used to modify the sensor of FIG. 1 or 2.

FIG. 6 shows the particle charging section 12 with a first flow sensor S1 at the inlet side, a second flow sensor S2 between the inlet and outlet sides and a third flow sensor S3 at the outlet side. The sensors in this example are all outside the ionization chamber, i.e. in the main air flow channel.

If the main air flow channel is annular around the ionization chamber, then sensors may be at only one angular position around the annulus, or at multiple positions around the annulus. The design does not need to be rotationally symmetric. Furthermore openings may be provided in the top or bottom of the ionization chamber, not only in the side walls.

Only one of S1 and S3 are in fact needed, since they should have the same flow reading (as it is a closed system). The second sensor S2 is generally aligned with the high voltage electrode tip, preferably slightly towards the inlet side so that it is positioned where the greatest flow reduction is experienced as shown in FIG. 4. For example it may be positioned at least 75% of the way along the section 12 between the inlet and the high voltage electrode tip. The distance d1 is the distance of the flow sensor from the inlet end of the ionization chamber (in particular the component parallel to the general flow direction) and the distance d2 is the distance of the tip of the ionization electrode from the inlet end of the ionization chamber. Hence, in one example d2>d1 and d1>0.75d2.

A second approach is to measure the differential pressure between the pressure $p_{cor}$ at the inlet end of the ionization chamber and the pressure $p_{exit}$ at the exit of the main air channel; $\Delta p = p_{cor} - p_{exit}$. When $\Delta p$ is negative this is indicative of a flow of the type shown in FIG. 4. This means there is a lower pressure in the ionization chamber induced by the large flow inside the chamber.

FIG. 7 shows the particle charging section 12 with a first pressure sensor P1 at the inlet end of the ionization chamber, at a corner (for measuring $p_{cor}$), and a second cor, pressure sensor P2 at the main channel exit (for measuring $p_{exit}$).

A second aspect relates to how to change the operation of the sensor when adverse flow conditions have been detected.

When the undesired flow conditions are detected, the current delivered to the high voltage electrode (the corona wire/needle electrode) may be reduced depending on the measured signals, i.e. the relative flow velocities or pressure differences.

Thus, the high voltage electrode drive voltage $V_{cor}$ is variable by a controller 27 as shown in FIGS. 1 and 2, and it may be adjusted making use of the information from the flow sensor arrangement. The flow rate thought the particle sensor may additionally or alternatively be controlled to influence the flow conditions.

The measures above relate to the detection and prevention of undesired flow conditions. It is also possible to design the system to prevent and reduce the occurrence of the undesired flow conditions.

Design rules for example include:

(i) Avoid asymmetric ion flow situations for example as induced by a metallic shield at the corona potential as shown in FIG. 4.

(ii) If a shield above the high voltage electrode tip is desired, then make it non-conducting. In this way the ion cloud is broadened which is advantageous.

(iii) Avoid grid openings which are not reachable by the ion flow, but for the gas flow only. FIG. 5 shows that the flow paths between the end channel openings do not pass the high voltage electrode 14, so that the flow through these channels is not contributing significantly to the ionization.

(iv) Instead of a transverse electrode, a horizontal corona wire may be used which spans the corona chamber in flow direction (inlet to outlet direction). This yields a broad ion cloud and a broad "ionic wind" distribution.

The effectiveness of a given design can be verified by numerical modeling of the electrostatics, the ion current continuity equation and the laminar flow in the main flow channel and the corona chamber.

Various examples have been given above for the sensor arrangement. The sensor arrangement may be considered generally to be a "flow sensor arrangement" in that the sensed signals are influenced by flow conditions, or it may be considered to be a "flow and/or pressure sensor arrangement". It may comprise flow rate sensors or pressure sensors or combinations of these, each of which provide measurements which relate generally to flow conditions. There may be sensor elements inside and/or outside the ionization chamber. One example has been given of a pressure sensor inside the chamber, but other examples may provide one or more flow rate sensors inside the ionization chamber. The aim is essentially to be able to distinguish between flows of the general type shown in FIG. 3 and those of the general type shown in FIG. 4. Various combinations of pressure sensors and flow rate sensors may be used to achieve this. Instead of (or as well as) sensing flow rate, it is possible to sense flow speed for example using a hot wire anemometer.

Two examples of precipitation section have been shown. However, there are other examples. For example, it is known to provide both a filter precipitation stage and an electrostatic stage so that multiple measurements are obtained— one with the electrostatic stage actuated and one with the electrostatic stage deactivated. This enables determination of both the number-averaged particle diameter and the particle number concentration.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A particle sensor, comprising:
   an input,
      wherein the input is configured to receive a gas flow,
      wherein the gas flow comprises entrained particles;
   an electrostatic particle charging section, the electrostatic particle charging section comprising an ionization electrode within an ionization chamber,
      wherein the gas flow passes past the ionization chamber and partially enters the ionization chamber,
      wherein the electrostatic particle charging section is configured to charge particles in the ionization chamber;
   a particle precipitation section,
      wherein the particle precipitation section is configured to precipitate the charged particles;
   a sensor circuit,
      wherein the sensor circuit is arranged to detect the precipitated particles to produce a sensor signal;
   a flow sensor arrangement,
      wherein the flow sensor arrangement is arranged to produce a flow signal,
      wherein the flow signal is representative of an amount of gas flow between the outside of the ionization chamber and the inside of the ionization chamber; and
   a controller,
      wherein the controller is arranged to control a gas flow rate through the particle sensor based on the flow signal.

2. The particle sensor as claimed in claim 1, wherein the flow sensor arrangement comprises an arrangement of flow rate meters.

3. The particle sensor as claimed in claim 2, wherein the arrangement of flow meters comprises a first flow meter outside the ionization chamber in the vicinity of an inlet end or an outlet end of the particle charging section, and a second flow meter outside the ionization chamber in the vicinity of a tip of the ionization electrode.

4. The particle sensor as claimed in claim 3, wherein the second flow meter is between the inlet end of the particle charging section and the tip of the ionization electrode.

5. The particle sensor as claimed in claim 1, wherein the flow sensor arrangement comprises an arrangement of pressure sensors.

6. The particle sensor as claimed in claim 5, wherein the arrangement of pressure sensors comprises a first pressure sensor inside the ionization chamber and a second pressure sensor outside the ionization chamber.

7. The particle sensor as claimed in claim 6, wherein the first pressure sensor is at the inlet end of the ionization chamber and the second pressure sensor is at the outlet end of the particle charging section.

8. The particle sensor as claimed in claim 1, wherein the precipitation section comprises a parallel-plate particle precipitation section.

9. The particle sensor as claimed in claim 1, further comprising a non-metallic shield in the ionization chamber.

10. The particle sensor as claimed in claim 1, wherein the controller is further arranged to control a drivel level applied to the ionization electrode based on the flow signal.

11. A particle sensing method, comprising:
receiving a gas flow, wherein the gas flow comprises entrained particles;
passing the gas flow through an electrostatic particle charging section,
wherein the electrostatic particle charging section comprises an ionization electrode within an ionization chamber,
wherein the gas flow is provided past the ionization chamber but partially enters the ionization chamber;
charging particles in the ionization chamber;
using a particle precipitation section to detect the charge of the precipitated particles to produce a sensor signal;
generating a flow signal, wherein the flow signal is representative of an amount of gas flow between the outside of the ionization chamber and the inside of the ionization chamber; and
controlling a gas flow rate through the particle sensor based on the flow signal.

12. The method as claimed in claim 11, further comprising measuring a first flow rate outside the ionization chamber in a vicinity of an inlet end or an outlet end of the particle charging section, and measuring a second flow rate outside the ionization chamber in a vicinity of a tip of the ionization electrode, wherein the signal is based on the relative sizes of the first and second flow rates.

13. The method as claimed in claim 11, further comprising measuring a first pressure inside the ionization chamber and a second pressure sensor outside the ionization chamber, wherein the signal is based on the difference between the first and second pressures.

14. The method as claimed in claim 13, further comprising measuring the first pressure at the inlet end of the ionization chamber and measuring the second pressure at the outlet end of the particle charging section.

15. The method as claimed in claim 11, further comprising controlling a drive signal applied to the ionization electrode based on the flow signal.

16. A particle sensor, comprising:
an input,
wherein the input is configured to receive a gas flow, wherein the gas flow comprises entrained particles;
an electrostatic particle charging section, the electrostatic particle charging section comprising an ionization electrode within an ionization chamber,
wherein the gas flow passes past the ionization chamber and partially enters the ionization chamber,
wherein the electrostatic particle charging section is configured to charge particles in the ionization chamber;
a particle precipitation section,
wherein the particle precipitation section is configured to precipitate the charged particles;
a sensor circuit,
wherein the sensor circuit is arranged to detect the precipitated particles to produce a sensor signal;
a flow sensor arrangement,
wherein the flow sensor arrangement is arranged to produce a flow signal,
wherein the flow signal is representative of an amount of gas flow between the outside of the ionization chamber and the inside of the ionization chamber; and
a controller,
wherein the controller is arranged to control a drive level applied to the ionization electrode based on the flow signal.

17. A particle sensing method, comprising:
receiving a gas flow, wherein the gas flow comprises entrained particles;
passing the gas flow through an electrostatic particle charging section,
wherein the electrostatic particle charging section comprises an ionization electrode within an ionization chamber,
wherein the gas flow is provided past the ionization chamber but partially enters the ionization chamber;
charging particles in the ionization chamber;
using a particle precipitation section to detect the charge of the precipitated particles to produce a sensor signal;
generating a flow signal, wherein the flow signal is representative of an amount of gas flow between the outside of the ionization chamber and the inside of the ionization chamber; and
controlling a drive level applied to the ionization electrode based on the flow signal.

* * * * *